United States Patent [19]

Wolfbeis

[11] Patent Number: 4,857,472
[45] Date of Patent: Aug. 15, 1989

[54] METHOD FOR CONTINUOUS QUANTITATIVE DETECTION OF SULPHUR DIOXIDE AND AN ARRANGEMENT FOR IMPLEMENTING THIS METHOD

[75] Inventor: Otto S. Wolfbeis, Graz, Austria

[73] Assignee: AVL AG, Schaffhausen, Switzerland

[21] Appl. No.: 198,759

[22] Filed: May 25, 1988

[30] Foreign Application Priority Data

May 27, 1987 [AT] Austria .................................. 1371/87

[51] Int. Cl.$^4$ ...................... G01N 33/00; G01N 21/76
[52] U.S. Cl. ..................................... 436/122; 436/172;
422/55; 422/58; 422/91; 250/458.1
[58] Field of Search ............................ 422/55, 58, 91;
436/122, 164, 172; 250/458.1, 459.1, 461.1

[56] References Cited

U.S. PATENT DOCUMENTS

| | | | |
|---|---|---|---|
| 3,845,309 | 10/1974 | Helm et al. | 250/365 |
| 4,180,739 | 12/1979 | Abu-Shumays | 250/458.1 X |
| 4,407,964 | 10/1983 | Elings et al. | 436/519 X |
| 4,433,060 | 1/1984 | Frenzel | 436/820 X |
| 4,476,870 | 10/1984 | Peterson et al. | 250/458.1 X |
| 4,549,807 | 10/1985 | Hoffmaster | 250/459.1 X |
| 4,580,059 | 4/1986 | Wolfbeis et al. | 250/459.1 |
| 4,587,101 | 5/1986 | Marsoner et al. | 422/56 |
| 4,608,344 | 8/1986 | Carter et al. | 422/58 X |
| 4,657,736 | 4/1987 | Marsoner et al. | 422/56 |

FOREIGN PATENT DOCUMENTS 2132348 4/1984 United Kingdom .

*Primary Examiner*—Michael S. Marcus
*Assistant Examiner*—Rebekah A. Griffith
*Attorney, Agent, or Firm*—Watson, Cole, Grindle & Watson

[57] ABSTRACT

In order to obtain a higher measuring accuracy and better selectivity in the optical quantitative analysis of sulphur dioxide in gaseous or liquid media, it is proposed that the medium to be analyzed be brought into contact with a fluorescent indicator which emits fluorescent light upon excitation and which is from the group of triphenylmethane dyes, and that the extent to which fluorescence is quenched by the $SO_2$ quencher be used as a measurable variable for quantitative determination of the content of sulphur dioxide in the medium.

11 Claims, 2 Drawing Sheets

METHOD FOR CONTINUOUS QUANTITATIVE DETECTION OF SULPHUR DIOXIDE AND AN ARRANGEMENT FOR IMPLEMENTING THIS METHOD

BACKGROUND OF THE INVENTION

This invention relates to a method for the continuous quantitative detection of sulphur dioxide in gaseous or liquid media.

DESCRIPTION OF THE PRIOR ART

In the last two decades sulphur dioxide has been recognized as one of the main causes of the so-called "acid rain" and its consequences, and of numerous other environmental problems. For this reason its quantitative detection is of prime importance in ecological analysis. Concentration may be measured with the use of continuous or discontinuous methods. Certain discontinuous techniques are based on the formation of dyes. Passing $SO_2$ through solutions of sodium tetrachloromercurate, for instance, will give rise to a complex which, together with formaldehyde and p-rosaniline, will produce a purple dye. The sampling work involved in this method requires considerable time and effort, including a lengthy delay between the actual sampling process and the final result of analysis. For these reasons the continuous method has proved much more suitable in environmental monitoring and process control.

Continuous measuring of the fluorescence of $SO_2$ itself has proved successful in practice, for example. With this technique the gas to be analyzed is excited by ultraviolet light within a range of wavelengths of 230 to 290 nm, and the fluorescence of $SO_2$ itself is observed in the range of 290 to 400 nm—a method described, for instance in U.S. Pat. No. 3,845,309. This technique is sensitive though not selective, as it will permit any other species producing fluorescence in this range of wavelengths to enter into the measurement. In addition, its results can easily be corrupted by the influence of smoke particles. It is not possible to determine the content of $SO_2$ in liquid samples, for instance in water, as in this excitation range the liquid samples also will give off fluorescence radiation, and contaminations of the liquid will increase fluorescence.

SUMMARY OF THE INVENTION

It is an object of this invention to propose a method which can be used in a simple manner for the continuous measuring of sulphur dioxide, without the drawbacks of the previous methods. Besides, the new method should be largely independent of other components of the sample which affect the test results in conventional techniques, and it should permit the analysis of liquid samples as well.

According to the invention this object is achieved by contacting the medium to be analyzed with a fluorescent indicator emitting fluorescence radiation upon excitation, from the group of polycyclic aromatic hydrocarbons and their derivatives, or that of triphenylmethane dyes, and by using the extent to which fluorescence is quenched by the sulphur dioxide quencher as a measurable variable for quantitative determination of the content of sulphur dioxide in the medium.

The method specified by the invention is based on the finding that $SO_2$ is capable of quenching the fluorescence of certain fluorescent indicators. In this instance the fluorescence of a fluorescent species other than sulphur dioxide is measured, contrary to the former techniques where it was the fluorescence of $SO_2$ itself that was under observation. Another difference is that in the previous method fluorescence rises along with a rise in $SO_2$ concentration, whereas there will be a decrease in fluorescence in the method described by the invention.

Among those fluorescent indicators whose intensity of fluorescence will be diminished by the influence of $SO_2$, are, above all, the polycyclic aromatic hydrocarbons and their derivatives, and the triphenylmethane dyes. These fluorescent indicators are exposed to an excitation radiation of 350 to 550 nm, which will produce considerably less interfering background radiation than the normal methods, since background radiation goes down as the wavelength increases. These fluorescent indicators are quenched in accordance with the law of Stern and Volmer, according to which the intensity of fluorescence of an indicator is highest ($I_o$) in the absence of its quencher and goes down to I when a quencher ($SO_2$ in this instance) is added. The concentration of the quencher is [$SO_2$]:

$$I_o/I = 1 + K_{sv} \cdot [SO_2]$$

$K_{sv}$'l being the Stern-Volmer constant, which depends on the quencher, the fluorescent indicator, the temperature, and the solvent and its viscosity.

The invention also provides that a fluorescent indicator from the group of alkyl-, amino-, hydroxy- or alkoxy-substituted derivatives of the polycyclic aromatic hydrocarbons be used, or that the triphenylmethane dye rhodamine 6G be used as a fluorescent indicator, and that in further development of the invention the fluorescent indicator be added to an $SO_2$-permeable polymer and a polymer membrane containing the indicator be formed, which should be brought into contact with the sample medium. This will further increase the selectivity of the method, as the membranes used basically are permeable to $SO_2$ only, which will protect the indicators from interfering substances.

In practice this is effected by dissolving a suitable fluorescent indicator, e.g., fluoroanthene, benzofluoroanthene, pyrene, diphenylanthracene or a similar polycyclic aromatic hydrocarbon, and also rhodamine 6G, in a suitable, $SO_2$-permeable polymer material, and by making a thin film out of this solution, which is coated onto a solid substrate, such as glass. The film is exposed to the liquid or gaseous sample medium, and the intensity of its fluorescence emitted upon excitation, is measured on the side facing away from the sample. Via the above equation the fluorescence intensity is related to the $SO_2$ concentration.

In addition to the possibility of dissolving the indicator in a polymer, the invention also provides that the fluorescent indicator may be immobilized on a substrate, preferably glass, in a known manner, either chemically or physically. This may be effected, for instance, by covalent bonding on a substrate, or by electrostatic immobilization. Techniques of chemical immobilization are state of the art and are described in various special publications.

In order to improve the solubility of indicators in the polymer solvents, which are more or less non-polar, it is best to render the fluorescent indicators polymer-soluble, as is described, for instance, in U.S. Pat. No. 4,587,101.

As the quenching of fluorescence by means of $SO_2$ may be strongly temperature-dependent, a further development of the invention provides that a temperature sensor be brought into thermal contact with the sample medium, in order to compensate the temperature dependency of the fluorescence quenching of individual fluorescent indicators, which will help take into account the influence of temperature. This is best achieved by adding a temperature sensor to the $SO_2$ sensor preferably in one and the same unit.

An arrangement for the performance of the method specified by the invention with the use of a fluorescent indicator on a substrate, which indicator is at least partly in contact with the medium to be analyzed and will emit fluorescent light upon excitation, is characterized by dissolving the fluorescent indicator in an $SO_2$-permeable membrane, preferably made from silicone rubber, polyvinylchloride or polyethylene. It is also possible, however, to select an arrangement in which the fluorescent indicator is directly immobilized on a substrate which should preferably be transparent to the excitation radiation and the fluorescence radation, without being embedded in a polymer.

In process control and when monitoring stack gases it is frequently impossible to take on-site measurements of fluorescence, as the measuring device cannot be directly installed in the sample path. In such instances a further development of the invention provides that the polymer membrane containing the indicator be located at the end of an optical waveguide. The excitation light is passed through a waveguide, i.e., to the end of the fiber which has been provided with the $SO_2$-sensitive polymer membrane, for example in the form of a small droplet or as a cylinder introduced into the core of the fiber. The fluorescent light given off by the indicator, whose intensity will serve to indicate the actual $SO_2$ concentration, is re-transmitted either through the same fiber or through another one. After any scattered light has been filtered out, e.g., by means of suitable optical filters, the light intensity is measured and the concentration of $SO_2$ is calculated by an appropriate mathematical evaluation procedure.

The fluorescence of certain dyes suitable for determining the $SO_2$ content can also be quenched by oxygen. Provided that the concentration of oxygen, or its partial pressure, always is constant, i.e., both during the calibrating and the measuring process, the quenching effect of oyxgen may be neglected. If the partial pressure varies, however, two sensors may be used, which contain different fluorescent indicators and react to the quenchers in different ways.

DESCRIPTION OF THE DRAWINGS

The invention will now be further described by way of example, with reference to the accompanying drawings, in which FIG. 1 gives a schematic view of an arrangement for the performance of the method according to the invention.

DETAILED DESCRIPTION OF THE PREFERRED EMBODIMENT

Figure 1:
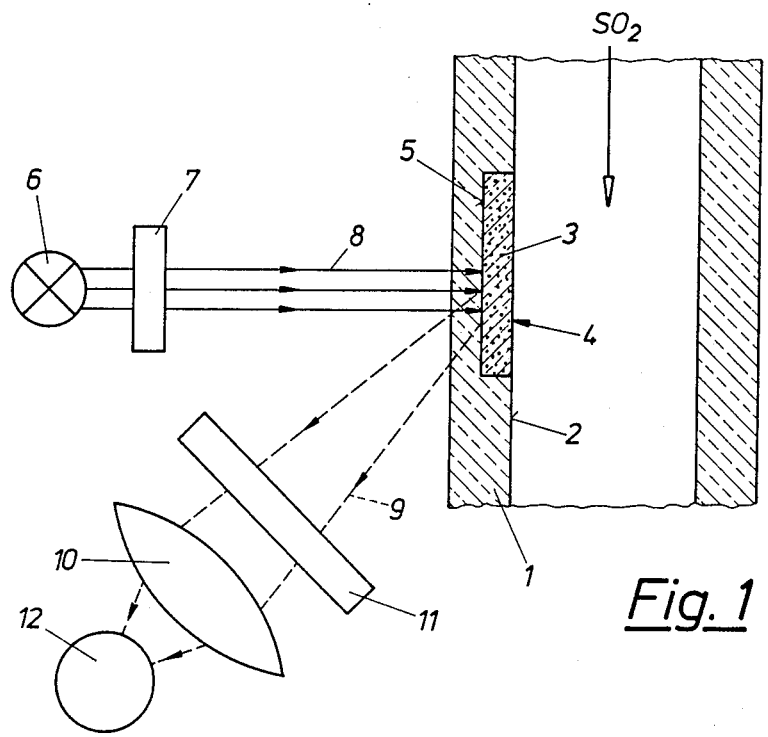

FIG. 1 shows an arrangement for the continuous determination of $SO_2$ in a pipe 1 through which the sample medium is passed, and which serves as a substrate for the $SO_2$-permeable polymer membrane 4 containing the indicator 3, and is in contact with the sample medium. The side 5 of the polymer membrane 4 facing away from the sample medium is subject to excitation radiation 8 from a light source 6 via a monochromator 7. The fluorescence radiation 9 emitted by the fluorescent indicator 3 of the polymer membrane 4 is passed, via a focusing lens 10 and a filter 11, to a detector 12 that is connected to an evaluation unit not shown here.

Figure 2:
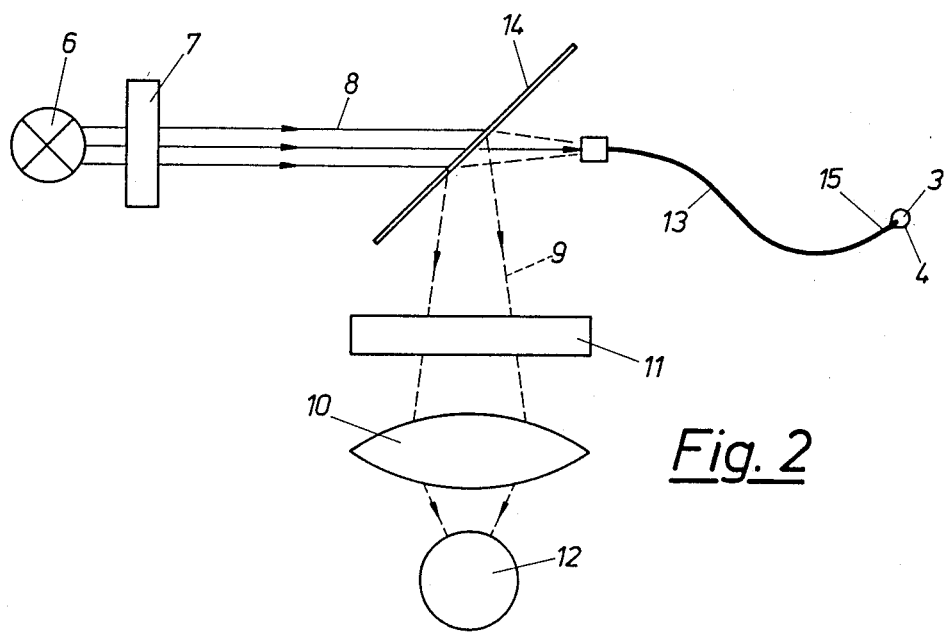
FIG. 2 shows another arrangement,
FIG. 3 a detail from FIG. 2,
FIG. 4 a variant of the detail in FIG. 3, and
FIG. 5 a diagram

FIG. 2 shows a set-up with an optical waveguide 13 into which the excitation radiation 8 is coupled via a dichroic mirror 14. The end 15 of the waveguide 13 carries the polymer membrane 4 containing the indicator. The dichroic mirror 14 directs the fluorescence radiation returning from the polymer membrane 4 towards the detector 12 together with the scattered excitation radiation. By interposing a filter 11 excitation and fluorescence radiations may be separated.

Figure 3:
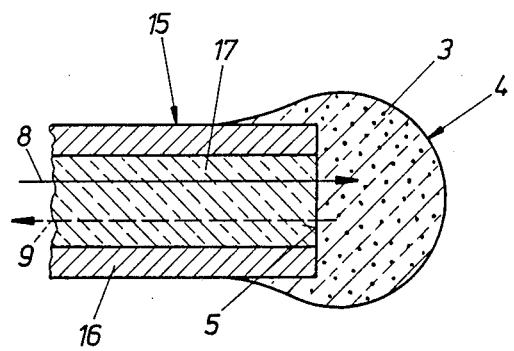
Figure 4:
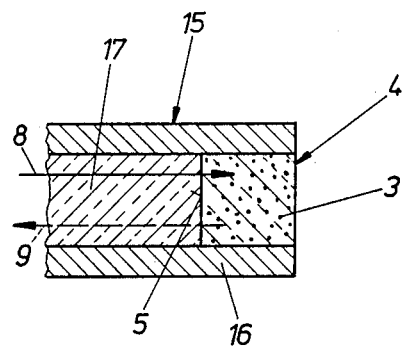

FIGS. 3 and 4 show variants of the set-up in which the $SO_2$-sensitive polymer membrane 4 containing the indicator is situated on the end 15 of the waveguide 13, the cladding of the waveguide being labelled 16 and its core 17.

Figure 5:
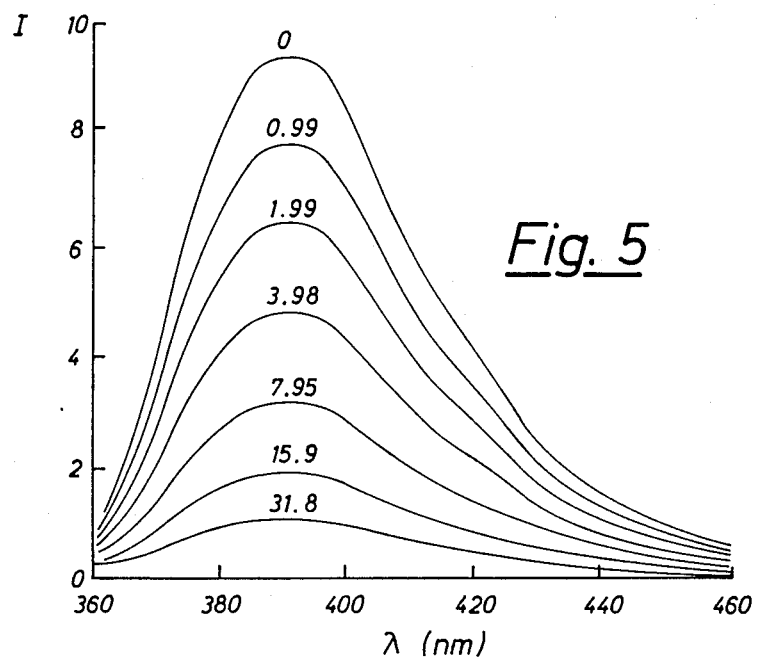

The diagram in FIG. 5, in which the wavelength $\lambda$ nm is plotted on the abscissa and the relative intensity I on the ordinate in unspecified units, shows the dependency of the fluorescence of pyrene (in methanol) on the amount of $SO_2$ present, the figures above the individual test curves referrring to millimol $SO_2$ per liter sample medium. The Stern-Volmer quenching constant $K_{sv}$ to be obtained from these figures is $238\ m^{-1}$. The corresponding values are $284\ m^{-1}$ for fluoroanthene, $225\ m^{-1}$ for benzofluoroanthene, $12.4\ m^{-1}$ for rhodamine 6G.

I claim:

1. A method for the continuous quantitative detection of sulphur dioxide in gaseous or liquid media, comprising the steps of bringing said medium to be analyzed into contact with a fluorescent indicator emitting fluorescence radiation upon excitation, said fluorescent indicator being selected from the group consisting of triphenylmethane dyes, and measuring the extent of fluorescence-quenching caused by sulphur dioxide contained in said gaseous or liquid media to enable a quantitative determination of the content of sulphur dioxide in said medium to be obtained.

2. A method according to claim 1, wherein said fluorescent indicator used in rhodamin 6G.

3. A method according to claim 1, wherein said fluorescent indicator is added to an $SO_2$-permeable polymer, and a polymer membrane containing said fluorescent indicator is formed and brought into contact with said medium to be analyzed.

4. A method according to claim 1, wherein said fluorescent indicator is chemically immobilized on a substrate.

5. A method according to claim 4, wherein said substrate is glass.

6. A method according to claim 1, including the step of bringing a temperature sensor into thermal contact with said medium to be analyzed to obtain a temperature value thereof, said temperature value being used to adjust the quantitative determination of sulphur dioxide content in said medium.

7. A method according to claim 1, wherein said fluorescent indicator is physically immobilized on a substrate.

8. A method according to claim 7, wherein said substrate is glass.

9. An arrangement for the continuous quantitative detection of sulphur dioxide in gaseous or liquid media, comprising a fluorescent indicator on a substrate, said fluorescent indicator being selected from the group consisting of triphenylmethane dyes and at least partly in contact with said medium to be analyzed and emitting fluorescent light upon excitation, wherein said fluorescent indicator is dissolved in an $SO_2$-permeable membrane.

10. An arrangement according to claim 9, wherein said $SO_2$-permeable membrane containing said fluorescent indicator is placed on the end of an optical waveguide.

11. An arrangement according to claim 9, wherein said $SO_2$-permeable membrane is made from silicone rubber, polyvinylchloride or polyethylene.

* * * * *